(12) United States Patent
Thilges et al.

(10) Patent No.: US 11,798,560 B1
(45) Date of Patent: Oct. 24, 2023

(54) RAPID EVENT AND TRAUMA DOCUMENTATION USING VOICE CAPTURE

(71) Applicant: CERNER INNOVATION, INC., Kansas City, KS (US)

(72) Inventors: Allison Michelle Thilges, Stilwell, KS (US); Neil Curtis Pfeiffer, Overland Park, KS (US); Eslie Rolland Phillips, III, Concord, NC (US); Geoffrey Harold Simmons, Parkville, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 777 days.

(21) Appl. No.: 16/720,644

(22) Filed: Dec. 19, 2019

Related U.S. Application Data

(60) Provisional application No. 62/783,681, filed on Dec. 21, 2018.

(51) Int. Cl.
*G10L 15/26* (2006.01)
*G10L 17/00* (2013.01)
*G16H 10/60* (2018.01)

(52) U.S. Cl.
CPC ............ *G10L 17/00* (2013.01); *G16H 10/60* (2018.01)

(58) Field of Classification Search
CPC ...... G10L 17/00; G16H 10/60; G06F 16/3329; G06K 9/6263
USPC ........................................................ 704/235
See application file for complete search history.

(56) References Cited

U.S. PATENT DOCUMENTS

| | | | |
|---|---|---|---|
| 10,347,117 | B1 | 7/2019 | Capurro |
| 10,951,762 | B1 | 3/2021 | Brandt et al. |
| 2008/0177537 | A1 | 7/2008 | Ash et al. |
| 2009/0100358 | A1 | 4/2009 | Lauridsen et al. |
| 2009/0138288 | A1 | 5/2009 | Benja-Athon |
| 2009/0268882 | A1 | 10/2009 | Lee et al. |

(Continued)

OTHER PUBLICATIONS

Final Office Action for U.S. Appl. No.16/720,632, mailed on Oct. 19, 2022, 31 pages.

(Continued)

*Primary Examiner* — Md S Elahee
(74) *Attorney, Agent, or Firm* — Kilpatrick Townsend & Stockton LLP

(57) ABSTRACT

Methods, systems, and computer-readable media for rapid event voice documentation are provided herein. The rapid event voice documentation system captures verbalized orders and actions and translates that unstructured voice data to structured, usable data for documentation. The voice data captured is tagged with metadata including the name and role of the speaker, a time stamp indicating a time the data was spoken, and a clinical concept identified in the data captured. The system automatically identifies orders (e.g., medications, labs and procedures, etc.), treatments, and assessments/findings that were verbalized during the rapid event to create structured data that is usable by a health information system and ready for documentation directly into an EHR. The system provides all of the captured data including orders, assessment documentation, vital signs and measurements, performed procedures, and treatments, and who performed each, available for viewing and interaction in real time.

20 Claims, 5 Drawing Sheets

(56) References Cited

U.S. PATENT DOCUMENTS

| | | | |
|---|---|---|---|
| 2010/0161353 | A1 | 6/2010 | Mayaud |
| 2011/0178931 | A1 | 7/2011 | Kia |
| 2014/0350961 | A1 | 11/2014 | Csurka et al. |
| 2015/0006199 | A1 | 1/2015 | Snider et al. |
| 2015/0142418 | A1 | 5/2015 | Byron et al. |
| 2015/0169827 | A1 | 6/2015 | LaBorde |
| 2016/0119305 | A1 | 4/2016 | Panchura et al. |
| 2017/0116373 | A1 | 4/2017 | Ginsburg et al. |
| 2018/0166076 | A1 | 6/2018 | Higuchi et al. |
| 2018/0308490 | A1 | 10/2018 | Lim et al. |
| 2018/0322110 | A1* | 11/2018 | Rhodes et al. ......... G16H 15/00 |
| 2018/0373844 | A1 | 12/2018 | Ferrandez-Escamez et al. |
| 2019/0121532 | A1 | 4/2019 | Strader et al. |
| 2019/0130073 | A1 | 5/2019 | Sun et al. |
| 2019/0206524 | A1 | 7/2019 | Baldwin et al. |
| 2019/0311807 | A1 | 10/2019 | Kannan et al. |
| 2022/0319646 | A1 | 10/2022 | Mukherjee et al. |
| 2022/0335942 | A1 | 10/2022 | Agassi et al. |

OTHER PUBLICATIONS

Non-Final Office Action for U.S. Appl. No. 17/132,859, mailed on Nov. 22, 2022, 30 pages.

Preinterview First Office Action of U.S. Appl. No. 16/720,641, mailed on Oct. 14, 2021, 7 pages.

* cited by examiner

RAPID EVENT AND TRAUMA DOCUMENTATION USING VOICE CAPTURE

CROSS-REFERENCE TO RELATED APPLICATIONS

This Application claims the benefit of priority to U.S. Provisional Application No. 62/783,681, filed on Dec. 21, 2018, entitled "Rapid Event and Trauma Documentation Using Voice Capture," the entirety of which is incorporated herein by reference.

BACKGROUND

Trauma is a fast-paced environment that includes many actors, many conversations, and many actions. Documentation during a trauma event is a specialized area because of the speed at which events are occurring. The fast pace of a trauma environment makes it very difficult to document the encounter. Many facilities still rely on paper documentation for trauma events (i.e., rapid events) because many electronic documentation systems do not lend themselves to such fast documentation. Many facilities also have trauma teams with team members trained as trauma recorders. This system continues to rely heavily on humans listening to actions of the team and manually documenting the information, increasing the possibility of missing or inaccurate documentation.

SUMMARY

Systems, methods and computer-usable instructions are provided for rapid event voice documentation. The rapid event voice documentation system displays orders, procedures, treatments, vital signs, measurements, assessments/findings, and the like, via voice capture and device integration, providing a fast, accurate rapid event documentation system. The system can utilize voice to capture verbalized orders, actions, and assessment information from voice data. The voice data captured by the system is automatically tagged with the name and role of the speaker (or any speaker identifier), a time stamp indicating a time the statement was spoken, a clinical concept identified in the data captured, and the like. Using natural language processing (NLP) software, the system automatically identifies orders (e.g., medications, labs and procedures, etc.), treatments, assessments/findings, and the like that were verbalized during the rapid event to create structured data that is usable by a health information system and ready for documentation directly into an EHR. The system provides all of the captured data including orders, assessment documentation, vital signs and measurements, performed procedures, and treatments, and who performed each, available for viewing and interaction at the time the event is occurring in real time.

BRIEF DESCRIPTION OF THE DRAWINGS

The present invention is described in detail below with reference to the attached drawing figures, wherein.

DETAILED DESCRIPTION

Figure 1A:
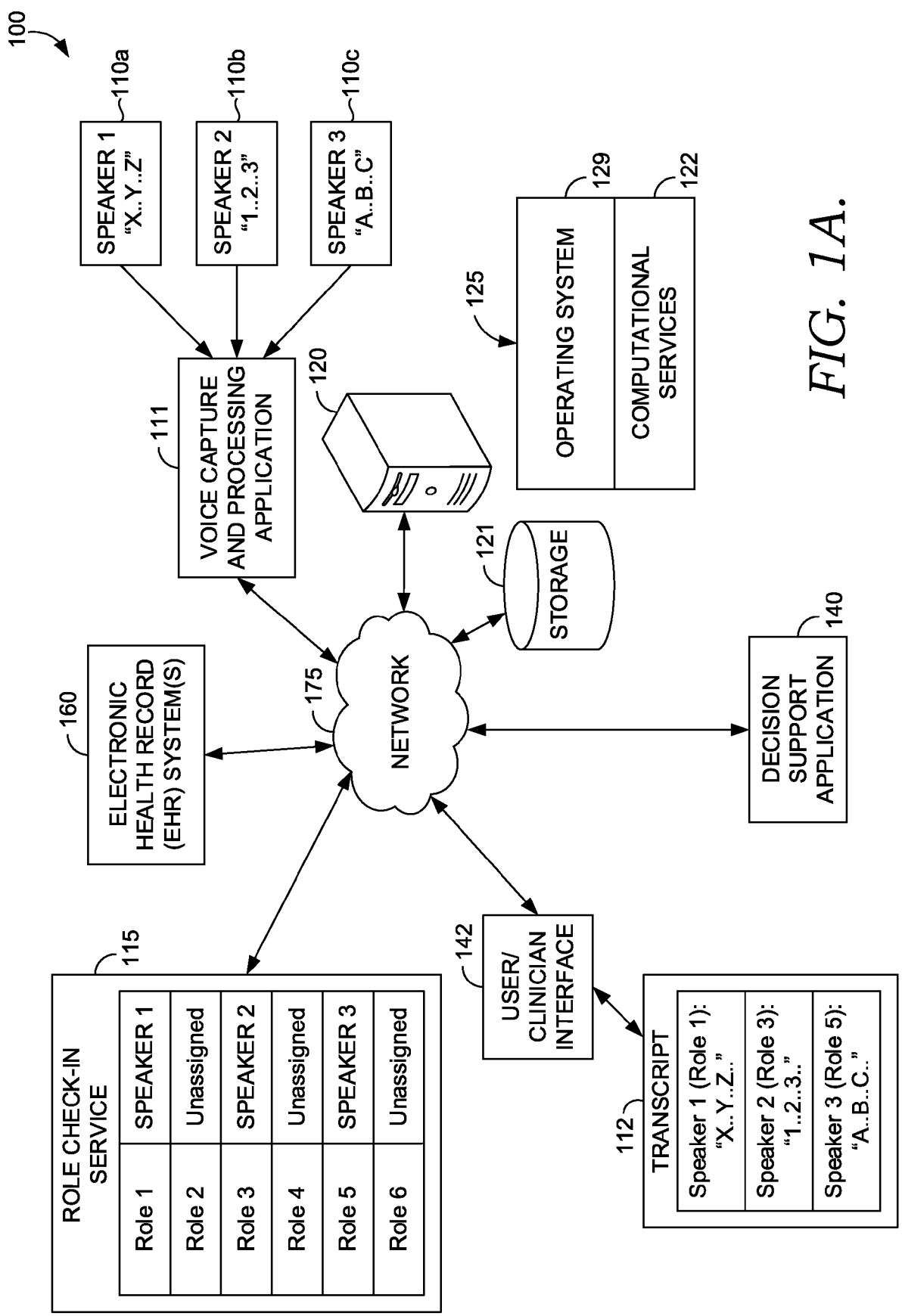
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, various technologies (NLP, voice recognition, speech recognition, artificial intelligence, machine learning, etc.) may be utilized to generate and provide documentation-type items from voice data associated with a rapid event. The system can capture voice data during the rapid event and, within the voice data, identify speakers, roles of speakers, time spoken, and clinical concepts. In-room positioning systems can also be utilized to capture location data or motion data during a rapid event (e.g., aid in the identification of the person speaking). A transcript of the voice data may be provided. The transcript may be searchable in real time and historically and may be broken into segments. The segments may be distinguished by speaker. Each segment is "tagged" with metadata including the speaker information and a role of the speaker (which may be indicated in any speaker identifier utilized by the system such as unique numerical strings associated with specific users), time stamp, and any clinical concepts identified within the statement. The segments are tagged based on predefined data within the system that matches the data coming in from the voice capture and the natural language processing. The metadata is then extracted by the system (for each segment) and utilized for rapid decision support processes and documentation. The metadata is utilized to classify the clinical concepts into one or more classification groups (e.g., orders, diagnoses, etc.). Thus, the system restructures the raw feed voice data and unstructured transcript into structured information that is usable by the health information system and, thus, provides for direct documentation into an electronic health record (EHR). The classification group is appended to the metadata so that each statement includes a classification group, if any, as well. Some statements may be identified as purely narrative and not include a classification group. Alternatively, a "narrative"

classification may be created and appended to metadata of such statements. The system verifies the structured data it generates with one or more sources including, but not limited to, the voice data, device data, EHR data, and the like. The information is displayed in real-time such that the generated structured data may be interacted with during the rapid event.

As used herein, the term "EHR" or "longitudinal EHR" refers to an electronic health record for an individual with documentation spanning across multiple encounters for the individual or at least one encounter prior to the current one for which the current electronic document is created. Accordingly, the documentation within the longitudinal EHR may be recorded at different times. The longitudinal EHR may also comprise at least some structured data. The data therein may be time and date stamped such that, in addition to providing the substance of those previous encounters, the longitudinal EHR provides a time line of the patient's care and, in some instances, one or more time series of physiological variables and clinical concepts related to the patient.

Accordingly, one aim of embodiments of this disclosure relates to providing rapid event voice documentation. Current technologies fail to capture, recognize, or incorporate into structured, usable data, valuable longitudinal patient information from voice data captured during a rapid event.

Electronic documentation of a trauma event is difficult in itself without introducing the complexity of providing documentation from voice data during the trauma event. Trauma documentation, today, still relies heavily on manual, non-electronic documentation. The trauma environment is too fast for any one person to properly electronically document in real-time for a variety of reasons including user interfaces that rely on the person listening, watching, and manually entering the data into highly organized, separate sections that perform better in a much slower documentation setting. Trauma events require all of the necessary data and documentation-type areas to be provided in a single view so a user can see and use it during a trauma event without navigating to separate documentation sections. It is also essential to have a comprehensive, singular view during a trauma event to have the whole encounter available. So many decisions in trauma events are made in seconds and then impact future decisions only moments later. Thus, it is necessary to see all of the information from the trauma event in a single view to provide appropriate care during the encounter. Effective, accurate electronic documentation of trauma events is problematic because of the fast pace of the multi-actor environment. Trauma events require quick processing for immediate documentation so that the event is part of the record going forward for use in newly developed events and for result trending that continues throughout the patient encounter. In trauma events, trauma teams need structured data for decision making in the next moment.

The present disclosure seeks to capture voice data and convert the raw, unstructured voice data to structured data consumable by a health information system. In particular, the present system seeks to translate raw, unstructured voice data to structured data that is ready to document into an EHR. The present disclosure provides the structured data as the speech is occurring.

Existing technology is unable to capture context from clinical voice conversations and certainly cannot capture context from voice data in rapid events. Rapid events include, for instance, multiple speakers all speaking at the same time, potentially. Capture of voice data adds another layer to this problem as there may be multiple individuals talking at the same time in a trauma event. For instance, one clinician may call for a medication while another is trying to stop a bleed and is shouting orders related to that issue at the same time as the medication order is vocalized.

Voice data in a clinical setting may further include many acronyms or short-hand clinical terms that would not be recognized by a typical voice assistant. Furthermore, clinical context is vastly different from typical "utterances" that are captured today. For instance, there are only a few ways to ask "what is the weather for today" and the response is predetermined but there are numerous ways to ask "how are you feeling today" and even more ways to respond to that question. Trauma is even more complicated than a non-trauma clinical setting because of the fast pace of the environment. Many things that may be spoken in a typical clinical setting are not completely vocalized in a trauma setting. For example, medication names may be shortened, abbreviations are used, etc.

Furthermore, many terms used in clinical conversations may be referred to as many different things. For instance, "cold" may refer to a chill (i.e., temperature) or an upper respiratory infection, which also goes by many different names. Even once a correct term is identified in a clinical conversation, it can then be associated with many different options. For example, "pneumonia" may trigger numerous coding options in ICD-10. To go through this analysis is not possible for today's voice assistants because of the vast clinical vocabulary. To go through this analysis in a rapid event situation such that structured data, from an unstructured source, is provided in real-time with the voice data is impossible for existing voice assistants. The present invention achieves this, with a high level of accuracy, by utilizing clinical ontologies specially created for clinical relationships and integration with an EHR system.

The accurate capture of data during a trauma event (rapid event) is crucial for proper care of a patient. Not having accurate, real-time documentation reduces the ability to trend results and identify result anomalies for enhanced quality of care. Rapid event documentation is provided herein to create an electronic system that automatically captures voice data at an accelerated pace and automates making the captured information available within the electronic system for rapid and accurate documentation. The data recorded in the rapid event is available in the EHR for result trending, result alerts, clinical decision support, billing, and submission to data registries.

In application, the systems described herein apply NLP and clinical ontologies to voice data to provide structured, usable output. Initially, voice data vocalized during a rapid event is captured. The voice data is the raw feed of data input to the system. Once captured, the voice data is transformed to text (e.g., a transcript) using speech recognition software. The transcript of the voice data may be provided in real-time. The speech recognition software may identify a pitch of a voice to identify who is speaking or voices could be pre-loaded into the system. If the system is not able to identify a speaker, unknown identifiers may be assigned to each speaker (e.g., Voice 1, Speaker 1, etc.) in the transcript, which can then be updated within the user interface and applied to all segments of that identifier. In-room positioning systems may also be used to identify who is in the room and where they are (e.g., camera, motion sensors, skeletal tracking technology, etc.).

The transcript may be broken into segments. The segments may be distinguished by speaker. Each segment is "tagged" with metadata including the speaker information, role of the speaker, time stamp, and any clinical concepts identified within the statement/segment. The metadata is utilized to classify the clinical concepts into one or more classification groups (e.g., orders, diagnoses, etc.). The classification group may be appended to the metadata so that each statement includes a classification group, if any, as well. As previously explained, some statements may be identified as purely narrative and not include a classification group. Alternatively, a "narrative" classification may be created and appended to metadata of such statements.

The metadata information includes, but is not limited to, speakers and roles associated with said speakers, time the voice data was spoken, clinical conditions, and the like. The speakers may be recognized by voice recognition technology. Alternatively, a trauma team may be known to the system to be on call during a specific time period and their voices may be pre-loaded into the system. The roles of the speakers may be known to the system by a stored speaker-role mapping. The concepts may be identified from the voice data utilizing clinical ontologies as described herein. In particular, a clinical ontology that is associated with a clinical condition identified in the voice data is retrieved, and one or more related clinical concepts (i.e., related to the clinical conditions), such as clinical findings, symptoms, problems, observations, medications, and procedures, are identified using the clinical ontology.

As used herein, a clinical ontology provides contextual relationships between a particular clinical condition and clinical concepts, such as evidence or symptoms of a clinical condition, treatment for the clinical condition (including procedures and medications), commonly co-existing conditions, risk factors for the clinical condition, and/or disqualifying evidence. The term "clinical ontology" as used herein is not intended to merely define a semantic hierarchy between concepts. Rather, a clinical ontology may provide one or more classifications comprising a set of clinical concepts that occur together within a patient's EHR as determined through one or more machine learning processes.

Clinical concepts, as used herein, generally refers to any clinical issue associated with a clinical encounter including, but not limited to, vital signs, a diagnosis, a problem, a medication, assessments/findings, etc. For instance, a clinician stating that a patient has shallow breath sounds and calling for a chest x-ray would include the clinical conditions of breath sounds and chest x-ray. Those may be mapped to several things using clinical ontologies including a classification group (e.g., assessments/findings, orders, tests, etc.).

The clinical concepts may be brought to a user's attention in a number of ways within the transcript. The clinical concepts may be highlighted within the transcript so they are easily identifiable. The clinical concepts may be extracted from the transcript and provided in a different area of the interface so that the concepts are easily accessible. A combination of the two may occur (e.g., highlight the terms and provide them in a separate listing area).

Additionally, the clinical concepts may be classified into one or more classification groups. Classification groups, as used herein, refers generally to groupings of clinical concepts. Standardized forms are utilized today with standard locations including problems, diagnoses, medications, symptoms, procedures, etc. The standardized form locations may be used as a guide for the system to use to generate classification groups. Standard electronic documentation guidelines may also be used as a guide to generate classification groups. By classifying the terms, the classification group may be appended to the metadata of the segment associated with the concept. Alternatively, the concepts may be organized graphically into segmented classification groups within the user interface such that orders are easily identified, tests are easily and separately identified, etc. The classifications can be editable by a user.

In some embodiments, multiple clinical conditions are extracted from the voice data and, thus, multiple classifications are identified (e.g., order, documentation, etc.). A separate ontology may be used for each condition to identify additional concepts related to one particular concept. Accordingly, when multiple conditions are extracted from voice data using NLP, multiple ontologies may be retrieved to identify concepts and classifications relevant to each condition.

Once populated and categorized, the items may be directly documented into an EHR. The items may be documented directly into a portion of the EHR that corresponds to the classification group generated by the present system. For instance, if a clinician orders a chest x-ray, the chest x-ray will be populated and classified as an order. Thus, it can be directly documented into an EHR order section. This direct documentation may be performed automatically by the system. The direct documentation may also be held for authorization and manual review by a user. Even when held for manual review, the system will have already generated all of the documentation in the correct section of the record, approval is simply provided by the user.

The data generated by the system (e.g., documentation items, etc.) may be validated against one or more validation sources. Validation sources may include, but are not limited to, a patient's EHR, another database tied to the EHR and/or health information system, the voice data, and the like. The validation sources are utilized to verify that the voice data captured and the data output generated are complete and accurate, in view of each other and additional sources. When a conflict is identified, the conflicting information may be provided in the single user interface provided by the system. For instance, if information in a patient's EHR indicates a conflict with a voice input, the voice input may be highlighted and the conflicting EHR information may be provided in conjunction with the voice input.

By way of a specific example, assume that a clinician, in a trauma event, calls for administration of Drug X but there is a note in the patient's EHR that indicates the patient is allergic to Drug X. Because of the real-time translation performed by the present system, the conflict is immediately identified upon capture and processing of the voice data. The conflict may be indicated in a user interface by way of a pop-up notification, an alert indicator (e.g., a graphical indicator such as an exclamation point), an audio indicator, and the like. In embodiments, the system may be linked with microphones in the trauma room such that the conflict is audibly provided, via a voice assistant, to the entire room. The conflicting information and/or the validation source of the conflicting data can also be provided.

By way of another example, assume that it was previously noted as a "clinical finding" that the patient is pregnant but now, later in the voice data, a drug is being ordered that cannot be administered to a pregnant woman. This would result in a conflict between the voice data and previously spoken voice data and immediate notification in near-real time of the spoken statement is provided.

The information may also be validated against the speaker's role. For instance, if an order is identified in the voice data but the speaker associated with that order is not a clinician, or not an ordering clinician, the system will identify that the input is not an order or not an authorized order. The system may tag the statement as narrative if not from a clinician or ask for further approval if context provides that the order may be intended but was not spoken by the ordering clinician. If the role of the user is verified, an order could be documented automatically into a patient's EHR and be sent through any other necessary system for completion of the order (e.g., order is sent directly to radiology to send up a portable chest x-ray) without any user input.

The information may also be validated against external device information. For instance, assume that a clinician states the patient's "blood pressure is dropping." The system intelligently retrieves the blood pressure information from a blood pressure device associated with the patient and/or the trauma room. If the information is validated, the corroborating information is integrated into the display such that the statement and the supporting evidence are simultaneously displayed. If the information is not validated (e.g., the blood pressure device indicates a normal blood pressure reading), a notification (visual, audio, etc.) may be provided alerting the team to the conflict. The notification may include the voice data and the conflicting device data. Conversely, the user interface may display an alert to the clinicians that the blood pressure is dropping based on information received from a blood pressure device associated with the patient and/or trauma room. The conflict may be indicated in a user interface by way of a pop-up notification, an alert indicator (e.g., a graphical indicator such as an exclamation point), an audio indicator, and the like. In embodiments, the system may be linked with microphones in the trauma room such that the conflict is audibly provided, via a voice assistant, to the entire room.

This intelligent analysis pulls in relevant information (conflicting or validating) to the voice data feed such that corroborating (or conflicting) validation data is provided with the voice data. Thus, the system goes further than identifying the conflict. The system intelligently provides why there is a conflict. This condensed display provides a system that is useable in rapid event documentation since the user does not have to navigate among a plurality of sections to validate information.

The system may also intelligently learn and be trained on voice data. Artificial intelligence may use an algorithm that builds over time using data such as orders that have been placed in the past on patients with the same or similar chief complaint, and same age, sex, weight, and clinical data to determine what order (synonym) is being used in a scenario.

The system may learn patterns based on role, speaker, time of day, etc. Based on a role or a speaker, the system can learn to change the display of the clinical term/name and dose of orders based on previous interactions. For instance, if a clinician always calls out an order using acronyms or short hand without stating the dose, the system can intelligently generate the clinical description of the order with the expected dose to what will be needed in the documentation. Or if speakers in role X always call an order a certain way, the system can learn and be trained on that behavior. The system can either generate a first order, recognize that it is typically changed to the full description, and automatically change it to the desired format or automatically generate the final order in the desired format without generation of a first order that will be changed. Additionally, a speaker may use a certain term in their orders that can be learned by the system to have a specific meaning. For example, a clinician may use "epi" in every case when referring to epinephrine. The system may automatically map the term "epi" to epinephrine. The system may utilize macros, as well, to provide this change.

The system may also adjust outputs based on additional information. For instance, a call for "epi" may typically be associated with a certain strength. However, the system may recognize that a patient is a pediatric patient (from their date of birth in their record) or that the patient is extremely overweight (e.g., from EHR data) and, thus, requires a different strength. The system may intelligently suggest a change to the spoken order or may automatically adjust the order and prompt a trauma documenter to confirm the changed order. Macros may be utilized in this instance. For example, macros may be defined for "epi" and specific clinical data, patient age, weight, sex, heart rate, blood pressure, respirations, heart rhythm, etc. and the system may use artificial intelligence to determine what order is being used in the specific event. An example narrative is provided below:

Captured Narrative:
Doctor Elizabeth: Give the patient Epi
Nurse Diane: 1/10000 epi going in IV
Nurse Emily: epi is in This narrative may result in the following structured documentation within a user interface:
Doctor Elizabeth: Give the patient epi [Epinephrine 1:10,000 0.1 mg/mL injection]
Nurse Diane: 1/10000 epi [Epinephrine 1:10,000 0.1 mg/mL injection] going in IV
Nurse Emily: epi [Epinephrine 1:10,000 0.1 mg/mL injection] is in A user interface may be provided with the entire voice narrative displaying names, roles, and time stamps of the unstructured data. A clinician can interact with the structured and unstructured data in real time to create ad hoc orders, assessment documentation, vital signs and measurements, performed procedures, and treatments, and quickly document who performed each action.

In embodiments, a user interface may be provided that includes at least one or more clinical concepts extracted from voice data. In embodiments, a user interface includes the one or more clinical concepts highlighted within a transcript of the voice data. In additional embodiments, the one or more clinical concepts are provided in one or more classification groups associated with documentation portions of a patient's record. For instance, a clinical concept that is identified as an order will be shown in the "order" classification group as it should be documented as an order within the patient's record. In embodiments, device readings may be provided in the user interface along with the voice data (e.g., transcript, clinical concepts, classification groups, or the like). The device data may be used as a validating source and may be provided in the single user interface. In embodiments, the views provided herein support reviewing the data both in real time and after the rapid event has ended and signing the entire narrative or selected data into the patient's record.

In embodiments, the system removes excess data from the transcript. This requires integration with an EHR system to identify relevance (or lack thereof) for identification of excess information. The system intelligently reviews the transcript, and the clinical concepts therein, to identify events relevant to the encounter. The system may be linked to a database or table that includes clinical concepts/conditions that are associated with certain data such that the concepts/conditions are linked to the associated data. For example, the database (or table) may indicate that for X event the system should look for things that indicate that event. Assume that a patient has a heart problem and is given a medication for said heart problem. Values would likely be present in the record that indicate the patient went into cardiac arrest during the trauma. Values are important to the administration of the medication and are linked in the database. The system can, thus, intelligently identify events within the trauma event and information relevant to those events. A weight or relevance may be assigned to each statement based on the relevance and evaluated against a predefined threshold. If the threshold is not satisfied, the information may be discarded or removed. If the threshold is satisfied, the information may be stored and maintained in the feed.

This removal of excess information may be performed automatically by the system or the system may prompt an authorized user to approve the removal of the excess information. If automatic, the system may still maintain the excess information for review by the user. If prompting a user for manual approval, the system will still have already tagged excess information as information that should be removed such that the work is already done by the system.

Referring now to the drawings in general and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural). Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

As shown in FIG. 1A, example operating environment 100 provides an aspect of a computerized system for compiling and/or running an embodiment for providing natural language processing or understanding of voice conversations. Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages, such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, the functions performed by these components, or the services carried out by these components may be implemented at appropriate abstraction layer(s), such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that, in some embodiments, functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems, and may be implemented in computer system 120. Similarly, EHR system 160 may perform functions for two or more of the EHR systems (not shown).

Continuing with FIG. 1A, network 175 may comprise the Internet, and/or one or more public networks, private networks, other communications networks, such as a cellular network or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health-related records, which may be stored on storage 121, and may further include one or more computers or servers that facilitate the storing and retrieval of the health records. In some embodiments, EHR system 160 and/or other records systems may be implemented as a cloud-based platform or may be distributed across multiple physical locations. EHR system 160 may further include record systems that store real-time or near real-time patient (or user) information, such as wearable sensor or monitor, bedside, or in-home patient monitors or sensors, for example. Although FIG. 1A depicts an example EHR system 160, it is contemplated that an embodiment relies on application 140 for storing and retrieving patient record information.

Example operating environment 100 further includes a user/clinician interface 142 and application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 may be communicatively coupled to EHR system 160 directly. An embodiment of application 140 comprises a software application or set of applications (which may include programs, routines, functions, or computer-performed services) residing on a client computing device, such as a personal computer, laptop, smartphone, tablet, or mobile computing device or application 140 may reside on a remote server communicate coupled to a client computing device. In an embodiment, application 140 is a Web-based application or applet and may be used to provide or manage user services provided by an embodiment of the technologies described herein, which may be used to provide, for example, semantic analysis on voice conversations. In some embodiments, application 140 includes or is incorporated into a computerized decision support tool. Further, some embodiments of application 140 utilize user/clinician interface 142.

In some embodiments, application 140 and/or interface 142 facilitate accessing and receiving information from a user or healthcare provider about a specific patient or set of patients, according to the embodiments presented herein. Embodiments of application 140 also may facilitate accessing and receiving information from a user or healthcare provider about a specific patient, caregiver, or population including historical data; healthcare resource data; variables measurements; time series information; reference information, including clinical ontologies; and relational databases, as described herein; or other health-related information, and facilitates the display of results of the enhanced language process as described herein.

In some embodiments, user/clinician interface 142 may be used with application 140, such as described above. One embodiment of user/clinician interface 142 comprises a user interface that may be used to facilitate access by a user (including a healthcare provider or patient) to an assigned clinician, patient, or patient population. One embodiment of interface 142 takes the form of a graphical user interface and application, which may be embodied as a software application (e.g., NLP application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application, which may take the form of an applet or app, or a set of applications usable to manage user services provided by an embodiment of the technologies described herein.

In some embodiments, interface 142 may facilitate providing output of the voice data; providing instructions or outputs of other actions described herein; providing notifications; and logging and/or receiving other feedback from the user/caregiver, in some embodiments.

Example operating environment 100 further includes computer system 120, which may take the form of one or more servers and which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers, and may be distributed across the other components of example operating environment 100. For example, aspects of application 140 or user/clinician interface 142 may operate on or utilize computer system 120. Similarly, a portion of computing system 120 may be embodied on user/clinician interface 142, application 140, and/or EHR system 160. In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as 122. Some embodiments of operating system 129 comprise a distributed adaptive agent operating system. Embodiments of services may run as local services or may be distributed across one or more components of operating environment 100, in the cloud, on one or more personal computers or servers such as computer system 120, and/or a computing device running interface 142 or application 140. In some embodiments, interface 142 and/or application 140 operate in conjunction with software stack 125.

Computational services 122 may perform statistical or computing operations such as computing functions or routines for determining confidence levels of extracted information, as further described herein. Computational services 122 also may include natural language processing services (not shown) such as Discern nCode™ developed by Cerner Corporation, or similar services. In an embodiment, computational services 122 include the services or routines that may be embodied as one or more software agents or computer software routines. Computational services 122 also may include services or routines for utilizing one or more models, including logistic models. Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a patient (or information for multiple patients), including raw and processed patient data; variables associated with patient diagnoses; and information pertaining to clinicians and staff, include user preferences. It is contemplated that the term "data" includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Example operating environment 100 can include a voice capture and processing application 111 that captures voice data within a predefined area (e.g., a trauma room, an operating room, etc.). As is shown for clarity, voice data 110*a*, 110*b*, and 110*c* is received by the voice capture and processing application 111. This data is analyzed, as described herein, and used to provide an output 112 at the user/clinician interface 142, as described in further detail at FIG. 2. Also shown for the sake of clarity is an exemplary role map 115 that is stored, for example, at network 175 and used by the application 140 to append voice data with relevant metadata (e.g., role information of the speaker).

Figure 1B:
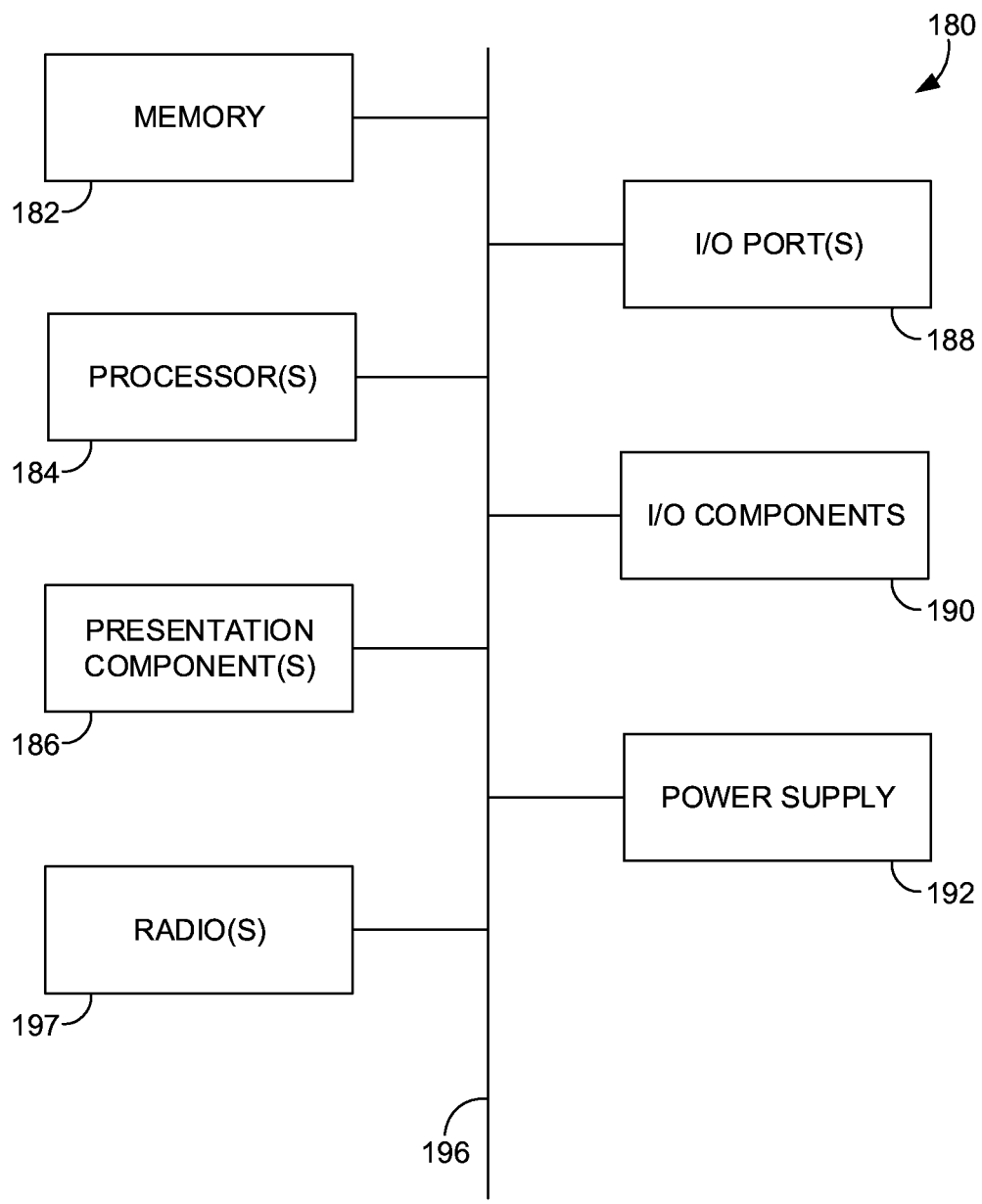

Turning briefly to FIG. 1B, there is shown one example embodiment of computing system 180 representative of a system architecture that is suitable for computer systems such as computer system 120. Computing device 180 includes a bus 196 that directly or indirectly couples the following devices: memory 182, one or more processors 184, one or more presentation components 186, input/output (I/O) ports 188, input/output components 190, radio 194, and an illustrative power supply 192. Bus 196 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1B and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 182 includes computer-storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 190. Presentation component(s) 186 present data indications to a user or other device. Exemplary presentation components include a display device, speaker, printing component, vibrating component, etc.

In some embodiments, computing system 194 comprises radio(s) 194 that facilitates communication with a wireless-telecommunications network. Illustrative wireless telecommunications technologies include CDMA, GPRS, TDMA, GSM, and the like. Radio 194 may additionally or alternatively facilitate other types of wireless communications including Wi-Fi, WiMAX, LTE, or other VoIP communications. As can be appreciated, in various embodiments, radio 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
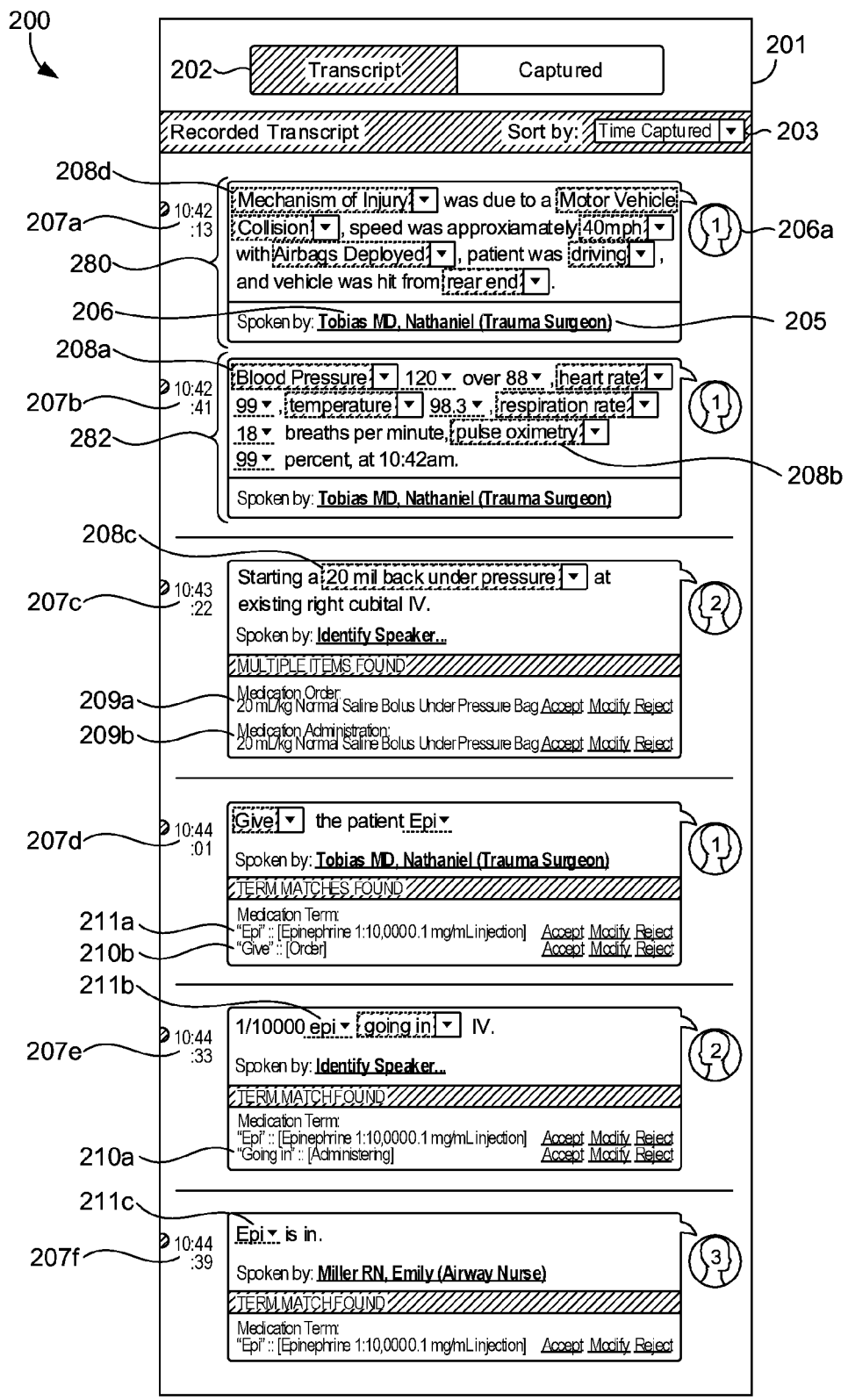
FIG. 2 depicts an exemplary graphical user interface transcript view in accordance with embodiments of the disclosure.
Figure 3:
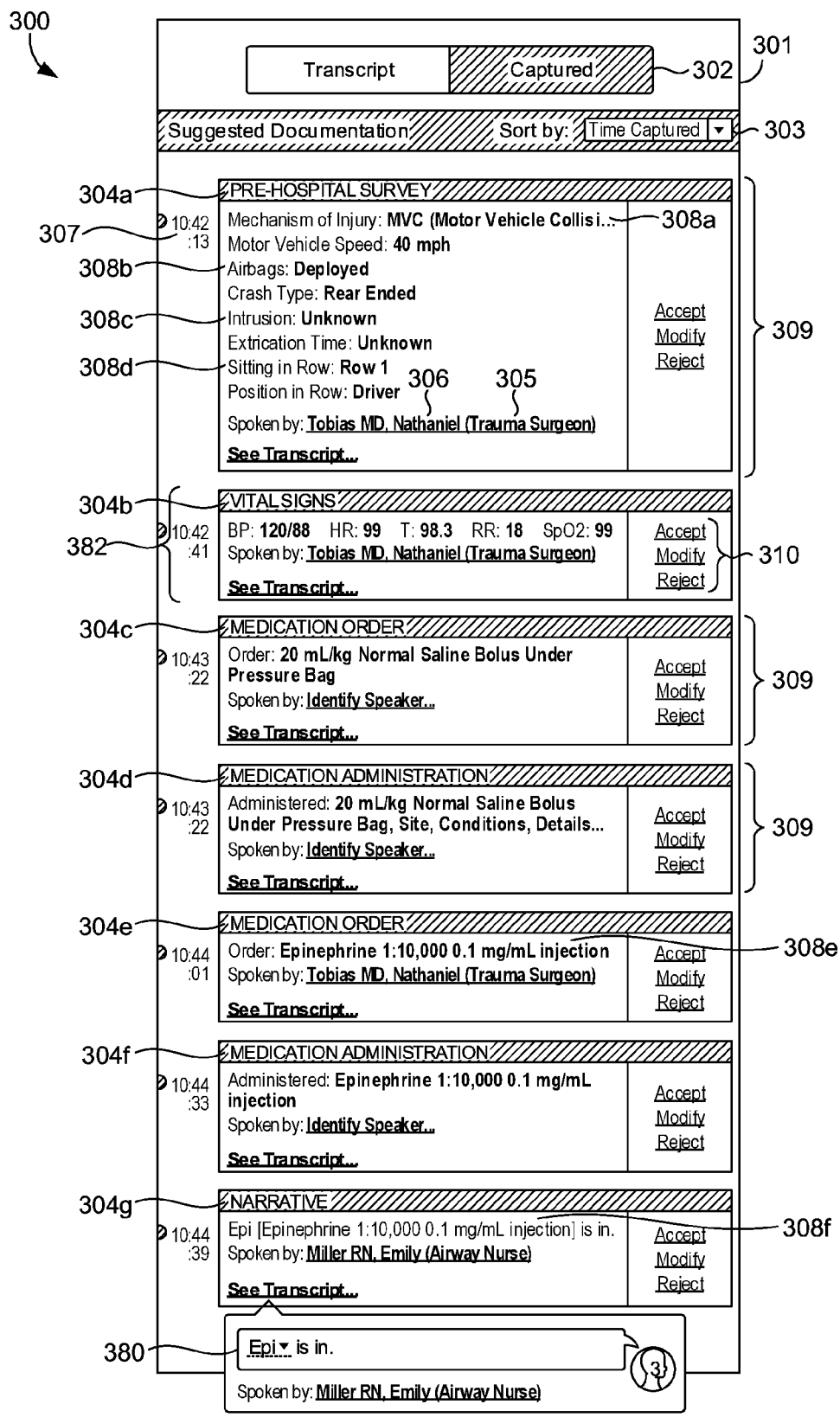
FIG. 3 depicts an exemplary graphical user interface structured view in accordance with embodiments of the disclosure.

Turning now to FIG. 2, an exemplary interface 200 of a transcript view 201 is provided. Initially, as shown, a transcript selector 202 is selected to provide the transcript view 201. Alternatively, a captured selector 302 (shown in FIG. 3) could be selected to provide the structured view 301 discussed below. The transcript view 201 includes the raw voice data captured by the system and appended with metadata. A sort feature is present (in both the transcript view 201 and the structured view 301) by selection of a sort selector 203 and 303.

Voice data can be captured and segmented by speaker, time stamp, clinical concept, and the like. As is shown in FIG. 2, a first segment 280 is captured and is separated from a second segment 282. Each segment, as shown, can include a time stamp (illustrated by time stamps 207a – 207f), a speaker (illustrated by speaker indicator 206), a role of the speaker (illustrated by role indicator 205), a graphical indication of the speaker (illustrated by graphical speaker indicator 206a). Additionally, each segment can include at least one clinical concept (illustrated by concept indicators 208a-208d). The system can intelligently change the display of the voice data to the suggested clinically documented item, for example. As is shown by indicators 209a and 209b, a spoken statement that one is "starting a 20 mil back under pressure ..." is automatically transformed to the structured suggested documentable item at indicator 209a (Medication Order: 20 mL/kg Normal saline bolus under pressure bag). Further, the next step for a medication order, which is administration, is also automatically populated at indicator 209b. This can be validated when voice data is captured that validates is was administered. Alternatively, it can be manually accepted by selection of one of the accept, reject, or modify icons associated with each documentable item. Illustrated at indicators 210a and 210b, the system can identify and/or learn that a certain speaker speaks in a specific way and process the voice data of that speaker accordingly. For instance, at indicator 210a, voice data for a speaker is captured as "going in" and automatically translated to "administering" for that speaker. At indicator 210b, similarly, voice data for a speaker saying "give" is automatically translated to "order" for the speaker. These automatic translations can be speaker-specific, clinical condition-specific, and the like. Further, as shown by indicators 211a-211c, the system can identify acronyms and shorthands and replace/map to the proper term. For instance, "epi" can be mapped to "epinephrine."

Figure 4:
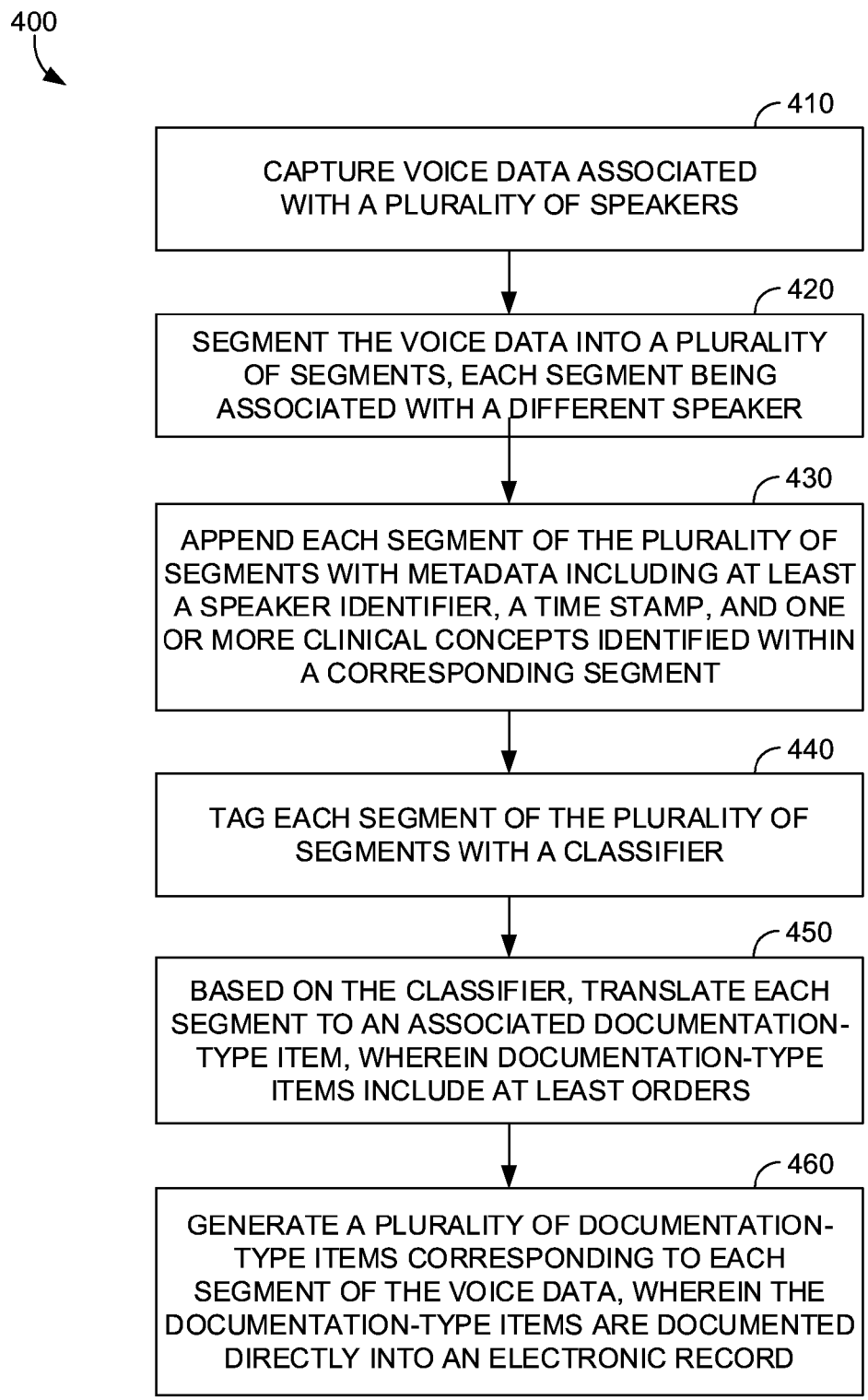
FIG. 4 depicts an exemplary method in accordance with embodiments of the disclosure.

Turning now to FIG. 4, a graphical user interface 300 of a structured view 301 is provided. The structured view 301 can include one or more documentation-type items such as items 309 ready to be documented in the record. Each of the documentable items can include a classification group (e.g., orders, vitals, narrative, administration, etc.) as shown at indicators 304a-304g. As with the transcript view 201 of FIG. 2, the role of the speaker 305, the speaker 306, and the time 307 can also be provided in the structured view 301. At any time within the structured view, a 'see transcript' indicator can be selected to provide a transcript portion 380 of the transcript related to the documentable item. The transcript portion 380 can include the speaker, the role of the speaker, a graphical indicator of the speaker, and the like.

Also illustrated in the structured view 301 is the ability of the system to take the voice data and translate it to structured data. Take, for example, the second segment 282 of FIG. 2. The voice data captured in that segment and the segment 282 itself are used to create documentation-type item 382. As is shown, the voice data indicating the vital signs has been transformed to structured data to put into a record. Each documentation-type item can include selectors to accept, modify, or reject the item, as shown by indicators 310 for documentation-item 382.

Turning now to FIG. 4, an exemplary method 400 is provided. Initially, at block 410, voice data associated with a plurality of speakers is captured. The voice data is segmented into a plurality of segments at block 420, where each segment is associated with a different speaker. At block 430, each segment of the plurality of segments is appended with metadata including at least a speaker identifier, a time stamp, and one or more clinical concepts identified within a corresponding segment. At block 440, each segment of the plurality of segments is tagged with a classifier. The classifier may be, for example, a classification group as described herein such as an order, a medication administration, a vital sign, and the like. At block 450, based on the classifier, each segment is translated into an associated documentation-type item, where documentation-type items include at least orders. At block 460, a plurality of documentation-type items is generated corresponding to each segment of the voice data. Each of the documentation-type items can be documented directly into an electronic record, such as a patient's electronic health record.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more non-transitory computer storage media storing computer-useable instructions that, when used by one or more computing devices, cause the one or more computing devices to perform a method comprising:
 capturing voice data associated with a plurality of speakers, each speaker of the plurality of speakers serving in a different role of a plurality of roles in a clinical environment;
 segmenting the voice data into a plurality of segments, each segment being associated with a different speaker of the plurality of speakers,
 for each segment of the plurality of segments:
  generating metadata for the respective segment, the metadata including an identifier that identifies the role served by the speaker associated with the respective segment;
  appending metadata to the respective segment; and generating, from the metadata appended to the respective segment, an item to be inserted into an electronic record, wherein the item is generated in-part based on the role served by the speaker associated with the respective segment; and inserting the items for the plurality of segments into the electronic record.

2. The media of claim 1, wherein the voice data is unstructured data.

3. The media of claim 1, wherein the items for the plurality of segments corresponds to structured data.

4. The media of claim 1, wherein the method further comprises receiving, from one or more sensors, location data of one or more speakers in a predefined area.

5. The media of claim 1, wherein the method further comprises generating a user interface including a real-time transcript of the voice data captured.

6. The method of claim 5, wherein the real-time transcript of the voice data captured includes the plurality of segments.

7. The media of claim 1, wherein the method further comprises validating the items for the plurality of segments against one or more validation sources.

8. The media of claim 7, wherein the one or more validation sources include an electronic health record.

9. The media of claim 7, wherein the one or more validation sources include data from an integrated device.

10. A system comprising:
one or more processors configured to:
capture voice data associated with a plurality of speakers, each speaker of the plurality of speakers serving in a different role of a plurality of roles in a clinical environment;
segment the voice data into a plurality of segments, each segment being associated with a different speaker of the plurality of speakers;
for each segment of the plurality of segments:
generate metadata for the respective segment, the metadata including an identifier that identifies the role served by the speaker associated with the respective segment;
append metadata to the respective segment; and
generate, from the metadata appended to the respective segment an item to be inserted into an electronic record, wherein the item is generated in-part based on the role served by the speaker associated with the respective segment; and
insert the items for the plurality of segments into an electronic record.

11. The system of claim 10, wherein the voice data is unstructured data.

12. The system of claim 10, wherein the items for the plurality of segments corresponds to structured data.

13. The system of claim 10, wherein the one or more processors are further configured to receive, from one or more sensors, location data of one or more speakers in a predefined area.

14. The system of claim 10, wherein one or more processors are further configured to generate a user interface including a real-time transcript of the voice data captured.

15. The system of claim 14, wherein the real-time transcript of the voice data captured includes the plurality of segments.

16. The system of claim 10, wherein the one or more processors are further configured to validate the items for the plurality of segments against one or more validation sources.

17. The system of claim 16, wherein the one or more validation sources include an electronic health record.

18. The system of claim 16, wherein the one or more validation sources include data from an integrated device.

19. A method comprising:
capturing voice data associated with a plurality of speakers, each speaker of the plurality of speakers serving in a different role of a plurality of roles in a clinical environment;
segmenting the voice data into a plurality of segments, each segment being associated with a different speaker of the plurality of speakers;
for each segment of the plurality of segments:
generating metadata for the respective segment, the metadata including an identifier that identifies the role served by the speaker associated with the respective segment;
appending metadata to the respective segment; and
generating, from the metadata appended to the respective segment, an item to be inserted into an electronic record, wherein the item is generated in-part based on the role served by the speaker associated with the respective segment; and inserting the items segment for the plurality of segments into an electronic record.

20. The method of claim 19, further comprising validating one or more of the voice data and the items for the plurality of segments against one or more validation sources, wherein the one or more validation sources comprises an electronic health record or an integrated device associated with a patient that is a subject of the voice data.

* * * * *